US007666638B2

(12) United States Patent
Andreoni et al.

(10) Patent No.: US 7,666,638 B2
(45) Date of Patent: Feb. 23, 2010

(54) SELENIUM-ENRICHED BIOMASS, METHOD FOR PREPARING THEREOF AND PROBIOTIC AND NUTRACEUTICAL PRODUCTS INCLUDING SAID BIOMASS

(75) Inventors: Vincenzina Andreoni, Milan (IT); Alberto Benedetti, Cernusco Sul Naviglio (IT); Enrica Canzi, Milan (IT); Salvatore Ciappellano, Milan (IT); Michela Fumagalli, Induno Olona (IT)

(73) Assignee: Bioman S.R.L., Turin (IT)

( * ) Notice: Subject to any disclaimer, the term of this patent is extended or adjusted under 35 U.S.C. 154(b) by 0 days.

(21) Appl. No.: 11/569,935

(22) PCT Filed: May 24, 2005

(86) PCT No.: PCT/EP2005/052361

§ 371 (c)(1),
(2), (4) Date: Dec. 1, 2006

(87) PCT Pub. No.: WO2005/118776

PCT Pub. Date: Dec. 15, 2005

(65) Prior Publication Data

US 2007/0258964 A1 Nov. 8, 2007

(30) Foreign Application Priority Data

Jun. 3, 2004 (EP) .................................. 04425408

(51) Int. Cl.
*C12P 1/04* (2006.01)
*C12P 13/04* (2006.01)
*C12P 13/12* (2006.01)

(52) U.S. Cl. ....................... 435/170; 435/106; 435/113; 435/252.9

(58) Field of Classification Search ....................... None
See application file for complete search history.

(56) References Cited

FOREIGN PATENT DOCUMENTS

| | | | |
|---|---|---|---|
| DE | 10206995 | A1 | 9/2003 |
| WO | 9221749 | A1 | 12/1992 |
| WO | 03078605 | A1 | 9/2003 |

OTHER PUBLICATIONS

Casa & Dobrogosz, Microbial Ecology in Health & Disease, 200, vol. 12, p. 247-285.*

Coeuret et al. , Lait 83, 2003, p. 269-306.*

Calomme et al., Biol Trace Elem Res., 1995, vol. 47, Abstract.*

Calomme et al., Journal of Applied Bacteriology, 1995, vol. 79, Abstract.*

V. Andreoni, et al., "Selenite tolerance and accumulation in the *Lactobacillus* species", Annals of Microbiology, 2000, pp. 77-88, vol. 50.

Heidi Annuk, et al., "Characterisation and differentiation of *Lactobacilli* by lectin typing", J. Med. Microbiol., 2001, pp. 1069-1074, vol. 50.

M.R. Calomme, et al., "Selenium and *Lactobacillus* species", Journal of Applied Bacteriology, 1995, pp. 331-340, vol. 79.

Ivan Casas, et al., "Validation of the Probiotic Concept: *Lactobacillus reuteri* Confers Broad-spectrum Protection against Disease in Humans and Animals", Microbial Ecology in Health and Disease, 2000, pp. 247-285, vol. 12.

C.N. Jacobsen, et al., "Screening of Probiotic Activities of Forty-Seven Strains of *Lactobacillus* spp. by In Vitro Techniques and Evaluation of the Colonization Ability of Five Selected Strains in Humans", Applied and Environmental Microbiology, Nov. 1999, pp. 4949-4956, vol. 65, No. 11.

J. Krooneman, et al., "*Lactobacillus diolivorans* sp. nov., a 1,2-propanediol-degrading bacterium isolated from aerobically stable maize silage", International Journal of Systematic and Evolutionary Microbiology, 2002, pp. 639-646, vol. 52, XP-002324276, with corresponding Appendix XP-002324277 (2 pages).

"*Lactobacillus reuteri*", Internet Article, XP002298288, http://www.ncbi.nlm.nih.gov/Taxonomy/Browser/wwwtax.cgi?id=1598, retrieved on Sep. 28, 2004.

L. Morelli, "In Vitro Selection of Probiotic *Lactobacilli*: A Critical Appraisal", Curr. Issues Intest. Microbiol., 2000, pp. 59-67, vol. 1, No. 2.

Gregor Reid, "The Scientific Basis for Probiotic Strains of *Lactobacillus*", Applied and Environmental Microbiology, Sep. 1999, pp. 3763-3766, vol. 65, No. 9, XP-000925091.

Kirsten Simpson, et al., "Characterization of *Lactobacilli* from Scotch malt whisky distilleries and description of *Lactobacillus ferintoshensis* sp. nov., a new species isolated from malt whisky fermentation", Microbiology, 2001, pp. 1007-1016, vol. 147, XP-002324316, with corresponding Appendix XP-002324317 (2 pages).

Rudi Vogel, et al., "Identification of *Lactobacilli* from Sourdough and Description of *Lactobacillus pontis* sp. nov.", International Journal of Systematic Bacteriology, Apr. 1994, pp. 223-229, vol. 44, No. 2, XP-002324316, with corresponding Appendix XP-002298480 (2 pages).

* cited by examiner

*Primary Examiner*—L Blaine Lankford
*Assistant Examiner*—Kade Ariani
(74) *Attorney, Agent, or Firm*—Rothwell, Figg, Ernst & Manbeck, P.C.

(57) ABSTRACT

The invention relates to a selenium-enriched biomass containing live microorganisms selected from the group consisting of *Lactobacillus reuteri, Lactobacillus ferintoshensis, Lactobacillus buchneri/parabuchneri* and combinations thereof, a method of preparation of the said selenium-enriched biomass, as well as food preparations, nutraceutical products and food supplements containing the said biomass. Moreover, new strains of lactobacilli are described that are able to concentrate selenium in very high amounts, and are therefore particularly useful for use in the method of the invention.

19 Claims, No Drawings

SEQUENCE LISTING

```
<160> NUMBER OF SEQ ID NOS: 8

<210> SEQ ID NO 1
<211> LENGTH: 20
<212> TYPE: DNA
<213> ORGANISM: artificial sequence
<220> FEATURE:
<223> OTHER INFORMATION: eubacteria universal primer 26f

<400> SEQUENCE: 1

agagtttgat cctgcctcag                                                20


<210> SEQ ID NO 2
<211> LENGTH: 20
<212> TYPE: DNA
<213> ORGANISM: artificial sequence
<220> FEATURE:
<223> OTHER INFORMATION: eubacteria universal primer 1495r

<400> SEQUENCE: 2

ctacggctac cttgttacga                                                20


<210> SEQ ID NO 3
<211> LENGTH: 357
<212> TYPE: DNA
<213> ORGANISM: Lactobacillus reuteri
<220> FEATURE:
<221> NAME/KEY: misc_feature
<222> LOCATION: (301)..(301)
<223> OTHER INFORMATION: n = c, a, g or t

<400> SEQUENCE: 3

cagtcgtacg cactggccca actgattgat ggtgcttgca cctgattgac gatggatcac      60

cagtgagtgg cggacgggtg agtaacacgt aggtaacctg ccccggagcg ggggataaca     120

tttggaaaca gatgctaata ccgcataaca acaaaagccg catggctttt gtttgaaaga     180
```

-continued

```
tggctttggc tatcactctg ggatggacct gcggtgcatt agctagttgg taaggtaacg    240

gcttaccaag gcgatgatgc atagccgagt tgagagactg atcggccaca atggaactga    300

nacacggtcc atactcctac gggaggcagc agtagggaat cttccacaat gggcgca       357


<210> SEQ ID NO 4
<211> LENGTH: 501
<212> TYPE: DNA
<213> ORGANISM: Lactobacillus reuteri
<220> FEATURE:
<221> NAME/KEY: misc_feature
<222> LOCATION: (54)..(54)
<223> OTHER INFORMATION: n = c, a, g or t

<400> SEQUENCE: 4

ttggtttaat tcgaagctac gcgaagaacc ttaccaggtc ttaacatctt gcgntaacct     60

tagagataag gcgttccctt cggggacgca atgacaggtg gtgcatggtc gtcgtcagct    120

cgtgtcgtga gatgttgggt taagtcccgc aacgagcgca acccttgtta ctagttgcca    180

gcattaagtt gggcactcta gtgagactgc cggtgacaaa ccggaggaag gtggggacga    240

cgtcagatca tcatgcccct tatgacctgg gctacacacg tgctacaatg gacggtacaa    300

cgagtcgcaa gctcgcgaga gtaagctaat ctcttaaagc cgttctcagt tcggactgta    360

ggctgcaact cgcctacacg aagtcggaat cgctagtaat cgcggatcag catgccgcgg    420

tgaatacgtt cccgggcctt gtacacaccg cccgtcacac catgggagtt tgtaacgccc    480

aaagtcggtg gcctaacctt t                                              501


<210> SEQ ID NO 5
<211> LENGTH: 304
<212> TYPE: DNA
<213> ORGANISM: Lactobacillus ferintoshensis
<220> FEATURE:
<221> NAME/KEY: misc_feature
<222> LOCATION: (251)..(251)
<223> OTHER INFORMATION: n = c, a, g or t
<220> FEATURE:
<221> NAME/KEY: misc_feature
<222> LOCATION: (288)..(288)
<223> OTHER INFORMATION: n = c, a, g or t

<400> SEQUENCE: 5

tcttggtatt gatgttaagt gcttgcattt aactgattta acattgagac gagtggcgaa     60

ctggtgagta acacgtgggt aacctgccct tgaagtaggg gataacactt ggaaacaggt    120

gctaataccg tataacaacc aaaaccacct ggttttggtt taaaagatgg cttcggctat    180

cactttagga tggacccgcg gcgtattagc ttgttggtaa ggtaacggcc taccaaggca    240

atgatacgta nccgacctga gagggtaatc ggccccattg ggactgcnac acggcccaaa    300

ctcc                                                                 304


<210> SEQ ID NO 6
<211> LENGTH: 448
<212> TYPE: DNA
<213> ORGANISM: Lactobacillus ferintoshensis

<400> SEQUENCE: 6

gctttgggtg ttacaaactc tcatggtgtg acgggcggtg tgtacaaggc ccgggaacgt     60

attcaccgtg gcatgctgat ccacgattac tagcgattcc aacttcatgt aggcgagttg    120

cagcctacaa tccgaactga gaacggcttt aagagattag cttgacctcg cggtttcgcg    180

actcgttgta ccgtccattg tagcacgtgt gtagcccagg tcataagggg catgatgatt    240
```

-continued

```
tgacgtcatc cccaccttcc tccggtttgt caccggcagt cttgctagag tgcccaactg    300

aatgctggca actaacaata agggttgcgc tcgttgcggg acttaaccca acatctcacg    360

acacgagctg acgacaacca tgcaccacct gtcattctgt ccccgaaggg aacgcctaat    420

ctcttaggtt ggcagaagat gtcaagac                                       448


<210> SEQ ID NO 7
<211> LENGTH: 192
<212> TYPE: DNA
<213> ORGANISM: Lactobacillus buchneri/parabuchneri

<400> SEQUENCE: 7

gcgtcttggt tattgatgtt aatgcttgca tttaactgat ttaacattga gacgagtggc     60

gaactggtga gtaacacgtg ggtaacctgc ccttgaagta ggggataaca cttggaaaca    120

ggtgctaata ccgtataaca accaaaacca cctggttttg gtttataaga tgtattcttg    180

ttataattta tg                                                        192


<210> SEQ ID NO 8
<211> LENGTH: 306
<212> TYPE: DNA
<213> ORGANISM: Lactobacillus buchneri/parabuchneri

<400> SEQUENCE: 8

aaggttacct caccggcttt gggtgttaca aactctcatg gtgtgacggg cggtgtgtac     60

aaggcccggg aacgtattca ccgtggcatg ctgatccacg attactagcg attccaactt    120

catgtaggcg agttgcagcc tacaatccga actgagaacg gctttaagag attagcttga    180

cctcgcggtt tcgcgactcg ttgtaccgtc cattgtagca cgtgtgtagc ccaggtcata    240

aggggcatga tgatttgacg acatccccac cttcctccgg tttgtcaccg gcagtctagc    300

tagagt                                                               306
```

SELENIUM-ENRICHED BIOMASS, METHOD FOR PREPARING THEREOF AND PROBIOTIC AND NUTRACEUTICAL PRODUCTS INCLUDING SAID BIOMASS

CROSS REFERENCE TO RELATED APPLICATION

This application is a 35 U.S.C. §371 National Phase Entry Application from PCT/EP2005/052361, filed May 24, 2005, and designating the United States.

The present invention relates to a selenium-enriched biomass, a method for preparing thereof, and probiotic and nutraceutical products containing the said biomass. The invention further relates to new strains of microorganisms belonging to the genus *Lactobacillus* suitable for use in the method of the invention.

Selenium is an essential element both for animals and for human beings, since it is included, mainly as selenocysteine, in the composition of important enzymes such as glutathione peroxidase and 5'-iodotyrosine deiodinase type I. The first enzyme catalyses the reduction of hydroperoxides preventing cellular degeneration and the formation of hydroxyl radicals; the second converts thyroxine to triiodothyronine, the active hormone that is essential for the metabolism of the thyroid hormones.

It has been observed that severe states of selenium deficiency in humans are correlated with increased risk of pathologies such as cancer, cardiovascular diseases, hypertension, stroke, and kidney and liver diseases. These deficiency conditions can, however, be corrected with a selenium-rich diet or by the administration of selenium in inorganic or organic form, for example by means of food supplements. Administration of selenium has also proved effective for counteracting the processes of cellular degeneration and formation of free radicals.

Utilization of selenates or selenites by the human body takes place through reductive processes with formation of selenides, which are then incorporated in non-conventional amino acids, in particular Se-methionine and Se-cysteine.

Many microorganisms (bacteria, yeasts and fungi) are able to grow in the presence of selenite and to reduce it to elemental selenium or to selenide to be incorporated as selenium-amino acids in proteins.

The ability to synthesize biomolecules containing selenium has been described in some lactic-acid bacteria of the genus *Lactobacillus* (Calomme et al. J. Appl. Bacteriol., 1995; Andreoni et al. Ann. Microbiol., 2000; 50, 77-88).

Strains of lactobacilli are therefore employed at present for probiotic purposes and the ability of these microorganisms to concentrate selenium in organic form may extend their use as supplements as well. V. Andreoni et al., Ann. Microbiol, 2000; 50, 77-88, describe the ability of some lactobacilli of various origins to accumulate selenium.

Now the present inventors have found, surprisingly, that microorganisms belonging to the species *Lactobacillus buchneri/parabuchneri*, *Lactobacillus ferintoshensis* and *Lactobacillus reuteri*, isolated from human faecal samples, are able to accumulate selenium in amounts that are on average 10 or more times greater than with the strains reported in the literature (Calomme et al. J. Appl. Microbiol., 1995; Andreoni et al. Ann. Microbiol. Enzimol., 2000). These species of *Lactobacillus* are therefore particularly suitable for the preparation of selenium-enriched biomass, especially with a view to the use of the said biomass as probiotic and/or nutraceutical agent.

A first object of the present invention is therefore a method of preparing selenium-enriched biomass, characterized in that the said biomass is obtained by (i) culturing microorganisms selected from the group consisting of *Lactobacillus reuteri, Lactobacillus ferintoshensis, Lactobacillus buchneri/parabuchneri* and combinations thereof in a nutrient culture medium comprising a selenium salt, such that the said microorganisms accumulate selenium; and (ii) separation of the selenium-enriched microorganisms from the culture medium.

With the method of the invention, a biomass is obtained comprising microorganisms containing a high amount of selenium accumulated in the cells, as is clear from the studies reported below. These studies have demonstrated, moreover, that a proportion of the selenium accumulated by the biomass is in organic form, in particular in the form of Se-methionine and Se-cysteine, which constitutes an advantage with a view to using the biomass as probiotic agent because selenium, in the form of Se-amino acids and incorporated in selenoproteins, is easily absorbed by the human body.

The method of the invention for the preparation of selenium-enriched biomass contemplates a first stage of fermentation, in which the microorganisms are cultured in a nutrient medium that is suitable for the growth of microorganisms of the genus *Lactobacillus* supplemented with a selenium salt, for example selenite, preferably sodium selenite. The nutrient medium is preferably a liquid medium containing sources of carbon, for example glucose, sucrose and/or lactose; sources of nitrogen, for example peptones, hydrolysates of casein, meat extracts and/or yeast extracts; inorganic salts; sources of trace elements and vitamins, for example corn steep liquor and the like.

Fermentation is preferably carried out at a temperature between 25° C. and 45° C., more preferably between 32° C. and 40° C. The pH value of the liquid medium is preferably between 2.5 and 8.0, more preferably between 3.5 and 7.5. The fermentation time is preferably between 6 and 40 hours, more preferably between 8 and 36 hours. Fermentation can be carried out in aerophilic, microaerophilic and/or anaerobic conditions.

After the fermentation stage, during which there is growth of the biomass and accumulation of selenium in the cells, the biomass obtained is separated from the culture medium, preferably by centrifugation or microfiltration, in such a way that the cells remain intact. The method of the invention therefore makes it possible to obtain a biomass of selenium-enriched microorganisms comprising live microorganisms.

If desired, the biomass obtained can then be submitted to an operation of lyophilization or drying, carried out according to conventional methods.

Furthermore, the present inventors isolated, from human faecal samples, three new strains of microorganisms belonging to the genus *Lactobacillus*, respectively designated LB2 BM, LB6 BM and LB26 BM, which proved particularly advantageous for use in the method of the invention, as they possess a high capacity for concentration of selenium, especially in the form of Se-methionine and Se-cysteine. These strains have been identified as belonging to the species *Lactobacillus reuteri* (LB2 BM), *Lactobacillus ferintoshensis* (LB6 BM) and *Lactobacillus buchneri/parabuchneri* (LB26 BM) (see example 11). Cultures of these strains of microorganisms have been deposited with the international depositary authority Deutsche Sammlung für Mikroorganismen und Zellkulturen (DSMZ, Braunschweig, Germany) under the Budapest Treaty on the international recognition of the deposit of microorganisms for the purposes of patent procedure:

| | LB2 BM | LB6 BM | LB26 BM |
|---|---|---|---|
| Accession number: | DSM 16143 | DSM 16144 | DSM 16341 |
| Date of deposit: | 17 Jan. 2004 | 17 Jan. 2004 | 5 Apr. 2004 |

As described previously, the selenium-enriched biomass obtainable by the method of the invention is particularly suitable for use as probiotic agent, as it contains high concentrations of selenium both in inorganic form and in organic form.

For this purpose, the biomass can be prepared in various forms. For example, it can be added to a food product, preferably milk or a dairy product such as yoghurt, to obtain a food preparation possessing probiotic activity. Alternatively, it can be used for the preparation of a composition possessing probiotic activity, for example a food supplement or a non-food preparation for oral administration, such as a nutraceutical preparation, in combination with suitable vehicles and/or excipients. For this purpose the biomass is preferably used in the form of a lyophilized or dried composition.

The bacterial load of the lyophilized or dried product to be used in the probiotic or nutraceutical composition is preferably at least $10^{10}$ CFU/g to $10^{11}$ CFU/g.

For preparing the lyophilized or dried composition the wet biomass is suspended in a liquid medium, for example water or sterile physiological solution, with addition of protecting agents such as skimmed milk, lactose, glucose, yeast extract, potato starch, sodium glutamate, inositol, sodium citrate, gelatin, maltodextrin, magnesium stearate, ascorbic acid, stearic acid and combinations thereof.

The lyophilized and/or dried composition is then diluted for the probiotic preparation with inert substances among those mentioned above for lyophilization, so as to obtain a bacterial load preferably of at least $10^9$ CFU/g.

The examples that follow are provided for purposes of illustration and are not intended to limit the scope of the invention in any way.

EXAMPLE 1

200 ml of MRS medium, to which 8 mg/l of Na-selenite ($Na_2SeO_3$) had been added, was sterilized in a 500-ml flask. A seed culture liquor of *Lactobacillus buchneri/parabuchneri* Lb26 BM-DSM 16341, previously grown for 18 hours at 37° C. without stirring, was inoculated in the flask in an amount of 5%. The culture was then left to grow for 24 hours in shakers at 80 rpm. On completion of culture, the biomass was harvested by centrifugation. The biomass was treated and analysed by the techniques described in example 9. The total selenium accumulated by the cells was 1.87 mg/$g_{d.w.}$; the amount of Se-methionine was 36.57 ng/$mg_{d.w.}$, and the amount of Se-cysteine was 135.70 ng/$mg_{d.w.}$.

EXAMPLE 2

*Lactobacillus ferinthoshensis* Lb6 BM-DSM 16144 was cultured as described in Example 1. After 24 hours of culture the total selenium accumulated was 1.1 mg/$g_{d.w.}$; the amount of Se-methionine was 12.63 ng/$mg_{d.w.}$, whereas that of Se-cysteine was 6.60 ng/$mg_{d.w.}$.

EXAMPLE 3

*Lactobacillus reuteri* Lb2 BM-DSM 16143 was cultured as described in Example 1. After 24 hours of culture the total selenium accumulated was 0.7 mg/$g_{d.w.}$; the amount of Se-methionine was 11.39 ng/$mg_{d.w.}$, whereas that of Se-cysteine was 83.78 ng/$mg_{d.w.}$.

EXAMPLE 4

*Lactobacillus buchneri/parabuchneri* Lb26 BM-DSM 16341 was cultured in a fermenter with 15L/10L of MRS medium to which 5% of Corn Steep Liquor (pretreated at pH 7.0 and at 100° C. for 15 min) and Na-selenite 8 mg/l were added, and then 4 additions of 5 mg/l every 4 hours starting from log6 (i.e. 6 hours after the start of fermentation). The fermenter was inoculated with 5% of seed at log16 and was maintained at pH 6.6 up to log20. The culture was stirred slowly (60 rpm) with air 0.51/1/min and was regarded as completed at log25. The biomass was harvested by centrifugation, obtaining 4.2 g/l of dry weight. Total selenium accumulation of 2.21 mg/$g_{d.w}$. was obtained.

EXAMPLE 5

*Lactobacillus ferintoshensis* Lb6 BM-DSM 16144 was cultured in a 15L fermenter as indicated in Example 4. 4.8 $g_{d.w}$. of biomass was obtained. The total selenium accumulated was 2.09 mg/$g_{d.w.}$

EXAMPLE 6

*Lactobacillus reuteri* Lb2 BM-DSM 16143, was cultured in a 15L fermenter as indicated in Example 4. 4.1 $g_{d.w}$. of biomass was obtained. The total selenium accumulated was 1.91 mg/$g_{d.w.}$

EXAMPLE 7

100 g of wet biomass equal to 28.1 $g_{d.w}$. of *Lactobacillus ferintoshensis* Lb6 BM-DSM 16144 was washed with sterile physiological solution and then resuspended in 520 ml of a solution containing ascorbic acid 3%, Na-glutamate 3%, inositol 4%, adjusted to pH 6.2 with NaOH, and was then lyophilized. 54 g of lyophilized composition with a bacterial load of $4.3*10^{11}$ CFU/g was obtained.

EXAMPLE 8

100 g of wet biomass equal to 28.1 $g_{d.w}$. of *Lactobacillus reuteri* Lb2 BM-DSMZ 16143 was prepared as in Example 7, resuspended at a concentration of approx. 40% (w/v) in an aqueous solution containing ascorbic acid 3%, Na-glutamate 3%. The suspension was dried with a "Spray-dryer" obtaining a dried composition with a bacterial load of $3.4*10^{10}$ CFU/g.

EXAMPLE 9

Methods of Analysis Selenium Accumulated by the Cells

The biomass obtained from examples 1, 2 and 3 was separated from the exhausted culture medium by centrifugation. The biomass was washed and the wash water was added to the exhausted medium. This was followed by determination of the amount of selenium in the culture medium at time zero ($T_0$) and after 24 hours of fermentation ($T_{24}$), as well as the amount of selenium accumulated by the cells. The results obtained are shown in the following table.

| STRAIN | Se in the culture medium time $T_0$ mg/L | Se in the culture medium time $T_{24}$ mg/L | Se removed mg/L | Effective Se accumulated by the cells mg/$g_{d.w.}$ | Se cysteine ng/$mg_{d.w.}$ | Se methionine ng/$mg_{d.w.}$ |
|---|---|---|---|---|---|---|
| Lb2 BM | 1.93 | 0.44 | 1.49 | 0.7 | 83.78 | 11.39 |
| Lb6 BM | 1.93 | 0.44 | 1.49 | 1.1 | 6.6 | 12.63 |
| Lb26 BM | 2.34 | 0.37 | 1.97 | 1.87 | 135.7 | 36.57 |

Determination of the Selenium Content

The amount of Se(IV) in the soluble fraction of the cytoplasm and in the particulate fraction was determined by potentiometric analysis at constant current. This analysis is performed using the Trace Lab PSU 20. This instrument determines trace elements even at a level below ppb and uses an extremely sensitive method of analysis. Three standard electrodes are used for the analysis: the glassy-carbon electrode, the platinum electrode and the calomel electrode.

Glassy-carbon electrode: this is the electrode that measures Se. Its tip is coated with a very thin film of mercury during the analysis.

Platinum electrode: this acts as a counter during electrolysis.

Calomel electrode: this is the reference electrode, it does not absorb metals, and contains saturated KCl.

Depending on the nature and concentration of the metal, the latter is differently deposited on the electrode in operation. The amount of metal deposited on the mercury film is proportional to the concentration of metal ions in the sample and to the electrolysis time (the amount of metal deposited on the electrode increases with increase in the electrolysis time).

The method used for determining the selenium content is the SE-ADD method, which contemplates the addition of 250 µl of the standard (5 ppm of Se). The reading range for selenium must be between 10 ppb and 100 ppb.

Preparation of Raw Cellular Extract

For determination of the content of Se-amino acids, first of all a raw cellular extract was prepared. For this, the cellular pellet was resuspended in the lysis solution (Tris HCl 50 mM-NaCl 0.3 mM) at pH 8.0, in the ratio 1 to 5 (1 g of pellet in 5 ml of lysis solution). For completing the lysis of the cell wall, a solution of lysozyme (50 mg/ml) was added at the amount of 20 µl/g of pellet. The mixture was stirred for 1 hour at 4° C. and was then submitted to 8 cycles of sonication (30-second cycles with 1 min pause in ice) (Bandelin HD 2070-U sonicator). The mixture was centrifuged at 15000 rpm (Beckman, JA20 rotor) for 1 hour at 5° C. to separate the soluble fraction of the cytoplasm from the particulate fraction (membranes and walls). After precipitation, the cytoplasmic proteins are analysed for the content of incorporated selenium and selenium-containing amino acids.

Determination of the Content of Se-amino Acids

For determining the content of Se-amino acids, 1 ml of distilled water was added to each sample, previously mineralized and lyophilized, and the solution thus obtained was adjusted to pH 7.5 with NaOH. Next, an aqueous solution of proteinase K was added to each sample in the ratio 1 to 10. The mixture was incubated at 37° C., with stirring, for 24 h. The proteins were precipitated by adding trichloroacetic acid to a final concentration of 10%. The suspension was centrifuged and the supernatant was collected and stored at −20° C. until it was used. The total selenium content was determined on one aliquot of the sample, and the amount of Se-methionine and Se-cysteine was determined on another aliquot using the LC/MS method described in: J. Agric. Food Chem., 2002; 50, 5722-5728.

EXAMPLE 10

Determination of the Resistance of the Lactobacilli to the Gastric Acidity and to the Bile The resistance to acidity of the strains of the present invention was tested by evaluating their survival after 90 minutes of contact with a gastric solution (J. App. Microb. 2001; 90, 268-278) at pH 2.00. The cells collected after 18 hours of growth at 37° C. in anaerobic conditions in MRS culture medium were resuspended in peptone water. Equal volumes of this bacterial suspension (0.1 ml) were added to 6 ml of gastric solution and to 6 ml of "control tube" solution, in order to reach a final concentration of approx. $1\times10^8$ CFU/ml. Both of the microbial suspensions were incubated at 37° C. for 90 minutes. The viable count was effected on samples taken at $T_0$ and after 90 minutes, by means of decimal dilutions and plating on MRS agar medium. The remaining volumes were centrifuged at 9500 rpm (Beckman, JA20 rotor) for 20 minutes at 5° C. in order to obtain the cells for suspending in the solution of biliary salts for determining the resistance to the bile. For this purpose the cells were resuspended in 6 ml of 0.1M phosphate buffer, pH 6.5, supplemented with peptone (1 g/L) and bile (3 g/L) and incubated at 37° C. for 3 h. At the same time, control cells were resuspended in 6 ml of the same buffer solution but in the absence of bile, and incubated as stated above. Determination of the bacterial load, as described above, was carried out on samples taken at $T_0$ and after 3 hours of exposure to the bile.

The protective effect of milk on the cells incubated in an acidic environment was evaluated on 2 strains, *L. reuteri* Lb2 BM and *L. buchneri/parabuchneri* Lb26 BM, which are sensitive, respectively, to exposure to biliary salts and to acidity. For this purpose the cells were inoculated in a solution of skimmed milk acidified to pH 2.0 and the number of CFU/ml was determined after exposure to this solution (pH 2.0 for 90 minutes) and to the solution of biliary salts (180 minutes).

| | Tolerance to gastric acidity | |
|---|---|---|
| | CFU/ml | |
| STRAIN | $T_0$ | After 90 min |
| Lb2 BM | $7.9\times10^7$ | $7.7\times10^7$ |
| Lb6 BM | $2.6\times10^6$ | $2.9\times10^2$ |
| Lb26 BM | $4.4\times10^6$ | $1.1\times10^2$ |

-continued

| Effect of biliary salts | | |
|---|---|---|
| | CFU/ml | |
| STRAIN | $T_0$ | After 180 min |
| Lb2 BM | $4.1 \times 10^7$ | $1.5 \times 10^4$ |
| Lb6 BM | $2.5 \times 10$ | $0.5 \times 10$ |
| Lb26 BM | $3.0 \times 10$ | $2.5 \times 10$ |

| Response of the strains to the presence of skimmed milk at pH 2.0 and bile | | | | |
|---|---|---|---|---|
| | CFU/ml | | | |
| | pH 2.0 | | Biliary salts | |
| STRAIN | $T_0$ | 90 min | $T_0$ | 180 min |
| Lb 2 BM | $8.3 \times 10^7$ | $4.1 \times 10^7$ | $1.2 \times 10^7$ | $6.8 \times 10^6$ |
| Lb 26 BM | $1.0 \times 10^7$ | $5.9 \times 10^6$ | $3.9 \times 10^6$ | $2.5 \times 10^6$ |

EXAMPLE 11

Identification of the Strains LB2 BM, LB6 BM and LB26 BM

The strains LB2 BM, LB6 BM and LB26 BM of the present invention were identified using the ARDRA technique (Amplified Ribosomal DNA Restriction Analysis) which contemplates amplification of the DNA region encoding the 16S rDNA gene using universal primers and then digestion of the amplified product obtained with restriction enzymes. The restriction fragments were then sequenced and the sequences obtained were aligned with known sequences for identifying the strain on the basis of the percentage homology.

Materials and Methods

Extraction of the DNA

The DNA was extracted from the cells of a broth culture in sterile MRS medium incubated at 37° C. for 24 h. Approximately 2 ml of broth culture was centrifuged at 13000 rpm for 5 minutes and the pellet collected was resuspended homogeneously in 1.85 ml of cell suspension solution; the following were added to the mixture: 50 µl of RNase mix and, after fast stirring, 100 µl of cell lysis/denaturing solution. The suspension was thermostatted at 55° C. for 15 minutes, supplemented with 25 µl of Protease mix, and held at 55° C. for 2 h. After adding 500 of salt-out mixture, 1.5 ml was held at 4° C. for 10 minutes and centrifuged at 13000 rpm for 10 minutes. 2 ml of TE (Tris-HCl 10 mM and EDTA 1 mM, pH 8, sterile) and 8 ml of 100% ethanol were added to the supernatant. The DNA strand, recovered with a glass rod, was supplemented with 500 µl of 70% ethanol and centrifuged at 11000 rpm for 30 minutes. It was held, after removing the aqueous phase, at 37° C. for 24 h, then resuspended in TE (approx. 200 µl) and stored at −20° C. until it was used. Extraction of the DNA was verified by electrophoresis on 0.7% agarose gel (w/v) in TAE 1X buffer.

Polymerase Chain Reaction (PCR)

Specific portions of the genome were amplified by the PCR technique. The PCR amplification reactions were carried out in a predefined reaction volume of 25 µl using sterile 200-µl Eppendorfs.

The reaction mixture consisted of:

DNA of the strain (template DNA), the template on which the polymerase chain amplification reaction is primed, used at a proportion of 1/25 of the final reaction volume;

a solution of $MgCl_2$ (1.75 mM) that supplies the $Mg^{2+}$ ions necessary for stabilizing the enzymatic activity of Taq-polymerase.

Two oligonucleotide primers (0.2 µM), one for the "forward" reaction (f) and one for the "reverse" reaction (r) which pair with the previously denatured complementary strands of DNA at complementary sequence points. The 3' free end of the primer supplies the starting point for the enzyme activity. The sequences of the primers vary depending on the region to be amplified and are given below.

A mixture of deoxyribonucleotide triphosphates (0.2 mM) (dNTP=dAPT+dCTP+dGTP+dTTP).

The heat-stable enzyme Taq-polymerase (Bioline, UK), which catalyses the reaction of synthesis of the new DNA on the starting template; the optimum temperature for its activity is 70° C.; the enzyme used is supplied at a concentration of 5 units/µl.

A buffer for the enzyme Taq-polymerase consisting of Tris-HCl (100 mM, pH 8.3) and KCl (500 mM), with the function of creating optimum ionic strength and pH for the enzyme reaction, added at a proportion of 1/10 of the final volume.

Sterile distilled water, representing the means by which the reaction takes place and making it possible to reach the desired volume.

The following precautions were taken to prevent contamination of the reaction with extraneous DNA:

preparation of the reaction mixture under a sterile hood with laminar flow;

sterilization of all the material used;

inclusion of a negative control, containing all the reactants except the template DNA, in every amplification reaction.

The reaction mixture, containing all the reactants specified above in suitable amounts, apart from the template DNA, was prepared in a 1.5-ml Eppendorf. The reaction mixture was then divided into aliquots in 0.2-ml Eppendorfs, to which the template was then added. The samples were quickly placed in ice to prevent the Taq-polymerase acting non-specifically.

The amplification results were verified by electrophoresis on 1.5% (w/v) agarose gel. If there are no bands in the electrophoresis profile of the negative control, it is considered that the reaction is not contaminated.

The table given below shows the concentrations of the reactants used in the reaction mixture for amplification of the 16S rDNA gene encoding the 16S subunit of the bacterial ribosomes.

The universal primers for eubacteria 27f 5'-AGA GTT TGA TCC TGC CTC AG-3' (SEQ ID NO:1) and 1495r 5'-CTA CGG CTA CCT TGT TAC GA-3' (SEQ ID NO:2) (Invitrogel) were used, which are located respectively at the 27th and 1495th nucleotide of the 16S rDNA gene of *E. coli*, permitting almost complete amplification.

| Reagent | Concentration |
|---|---|
| Buffer | 1.00 × |
| $MgCl_2$ | 1.75 mM |
| $dNTP_s$ | 0.2 mM |
| forward primer | 0.2 µM |

-continued

| Reagent | Concentration |
|---|---|
| reverse primer | 0.2 μM |
| Taq-polymerase | 2.0 U* |
| DNA | 2.0 μl |

*The Unit is defined as the amount of enzyme that incorporates 10 ng of dNTP in 30 minutes at a temperature of 74° C. The enzyme is heat-stable and catalyses the reaction of synthesis of the new DNA on the starting template.

The test tubes containing the reaction, immediately after preparation, were placed in the thermal cycler for PCR GeneAmp PCT System 2400 (Perkin Elmer) applying the following thermal cycle: denaturation at 95° C. for 3 minutes; 35 cycles at 94° C. for 1 minute; 55° C. for 1 minute; 72° C. for 2 minutes; then a final extension phase at 72° C. for 15 minutes.

The results of amplification were verified by electrophoresis in 1.5% (w/v) agarose gel in TAE 1X buffer. Any amplification of the 16S rDNA can be detected by the presence of an amplification band of approx. 1500 nucleotides. The molecular weight of the DNA, corresponding to the band visible on the gel, is found by comparing with the bands produced by the run of the Ladder 100 bp Plus, a mixture of DNA fragments with lengths that are multiples of 100 bp.

Digestion with Restriction Enzymes

The amplified product obtained was digested with the restriction enzymes HhaI, HinfI, Afa.

The reaction of digestion of the 16S rDNA of each strain was carried out in a volume of 10 μl using the following reagents:

- amplified DNA, in variable amounts depending on the intensity of the amplification band;
- specific buffer for each enzyme 10× (Amersham Biosciences);
- restriction enzyme (Amersham Biosciences) (10 U/μl);
- MilliQ water for bringing the volume up to 10 μl.

The following table shows the amounts of the reagents used in the reaction mixture for digestion of the 16S rDNA fragment.

| Reagents | Amounts |
|---|---|
| DNA | varies depending on the intensity of the amplification band |
| enzyme (10 U/μl) | 1 μl |
| Buffer | 1 μl |
| Water | q.s. |
| final volume | 10 μl |

The reagents were placed in Eppendorfs and incubated at 37° C. for 12 h. The samples were stored at −20° C. and were then analysed by electrophoresis on 3% (w/v) agarose gel in TAE 1X buffer using Ladder 50 bp for evaluating the weight of the bands characterizing the samples.

Enzymatic digestion of the 16S rDNA creates a profile formed from various bands of different molecular weight as a function of the sites recognized by the enzyme present on the sequence analysed. The total of the bands must not exceed the length of the amplified fragment (1500 bp).

Gel Electrophoresis of the DNA

The operating conditions contemplate the use of a horizontal agarose gel in Tris-acetate-EDTA (TAE) running buffer consisting of: Tris-base 0.04 M, glacial acetic acid 0.02 M, $Na_2$-EDTA 0.001 M, pH 8. The run takes place at room temperature, maintaining a constant voltage between 90 V and 110 V as a function of the dimensions of the gel. The run is stopped when the DNA fragments have covered approx. ⅔ of the length of the gel.

The concentration of the agarose varies from 0.7% to 3% depending on the size of the DNA molecules that are to be separated:

- 0.7% for verifying extraction of the DNA
- 1.5% for verifying amplification of the 16S rDNA
- 3% for verifying digestion of the DNA with restriction enzymes.

The gel for the electrophoresis run was prepared by dissolving the agarose in TAE 1X buffer. Before it was loaded into the wells, the DNA was mixed at a ratio of 1:5 (v/v) with the gel loading solution consisting of sucrose 40% (w/v), bromophenol blue 0.05% (w/v), EDTA 0.1 M pH 8, and sodium dodecylsulphate (SDS) 0.5% (w/v).

The first and the last well of the gel were loaded with markers of known molecular weight, containing discrete bands of DNA, which are used for evaluating the length of the samples, expressed in base pairs (bp). On completion of the run, the marker reveals an electrophoresis profile with discrete bands, corresponding to known lengths of DNA.

When the bands have travelled approx. ⅔ of the gel, the latter is immersed in a 0.5 mM solution of ethidium bromide (Sigma) away from the light for 15-30 min. The gel is then washed in distilled water for about 15 min and photographed in the light of a UV transilluminator connected to a Gel Doc image acquisition system (Biorad).

Purification of the PCR Products

The QIAquick gel extraction kit protocol was used for purification of 70 bp-10 kb of the amplification products. The purified product (approx. 450 μl) was stored at −20° C., in a 2 ml microtube, until it was used.

Precipitation of the DNA

Na acetate (pH 5; 3 M) was added to the purified product at a proportion of 1/10 of the volume of the DNA obtained and then 100% ethanol was added at a proportion of 2.5 volumes of the DNA.

It was centrifuged at 4° C. for 20 minutes at 14000 rpm to remove the supernatant. The precipitate, after addition of 500 μl of 70% ethanol, was centrifuged at 4° C. for 15 min. Following removal of the supernatant, the ethanol remaining in the Eppendorf was evaporated in a thermostat at 37° C. for about 15 min and then under a hood. The precipitate was resuspended in 23 μl of TE pH8 and stored at 4° C. until it was used.

Quantification of the DNA

The amplified products were quantified by comparing the fluorescence of the sample with that of the marker at known concentration by means of the Gel Doc image acquisition system (Biorad).

An 1.5% agarose gel was prepared. The wells were loaded with two mixtures of markers of known molecular weight, formed respectively from:

1) 20 μl marker Low Range Mass Ruler™ (MBI Fermentas)

2) 10 μl marker Low Range Mass Ruler™ (MBI Fermentas).

2 μl of the sample DNA was mixed with 2 μl of bromophenol blue and 6 μl of MilliQ water. 10 μl of mixture was loaded on the gel.

Sequencing

The sequencing reaction was carried out by PCR amplification using 200 ng of PCR product, 6 pmol of primers 27f and 1495r (Invitrogen), 4 μl of buffer (2.5X) and 4 μl of "DyeTerminator" premix (Amersham Biosciences), containing a mixture of nucleotides labelled with fluorochromes. The final volume is 20 μl. A Biometria thermal cycler was used for the amplification reaction, applying the following thermal cycle: denaturation at 95° C. for 2 min; 25 cycles at 94° C. for 30 seconds, 55° C. for 30 seconds, 60° C. for 4 min; then a final extension phase at 60° C. for 15 minutes. Next, purification of the labelled nucleotides was carried out: the QUICK RUN samples were centrifuged and transferred to 1.5-ml Eppendorfs where 2 μl of Na acetate and 80 μl of 100% ethanol were added. The whole was centrifuged at 13000 rpm for 5 minutes and, once the supernatant had been removed, 1 ml of 70% ethanol was added. After centrifugation at 13000 rpm for 5 minutes the supernatant was removed and the residual ethanol was evaporated, placing the mixture under a hood for 15 minutes. The residue was resuspended in approx. 13 μl of Mega BAC buffer and it was stirred on a vortex for 20 seconds. The QUICK RUN was centrifuged, the samples were transferred to 1.5-ml Eppendorfs and then loaded in an Applied Biosystem 310A sequencer, where an Applied Biosystem capillary electrophoresis run was carried out.

Search for Homologies

The sequences obtained were aligned with sequences present in the GenBank and EMBL databases using the programs Fasta3 and GeneSteam Align. The sequences used for each strain, the number of bases sequenced, the percentage homology and the species to which each strain was ascribed are shown below.

LB2 BM-DSM 16143
- *Lactobacillus reuteri*
- number of bases sequenced 860
- % homology: 99.5
- LB2 BM forward (SEQ ID NO:3)
- LB2 BM reverse (SEQ ID NO:4)

LB6 BM-DSM 16144
- *Lactobacillus ferintoshensis*
- number of bases sequenced 748
- % homology: 98.9
- LB6 BM forward (SEQ ID NO:5)
- LB6 BM reverse (SEQ ID NO:6)

LB26 BM-DSM 16341
- *Lactobacillus buchneri/parabuchneri*
- number of bases sequenced 485
- % homology: 99.4
- LB26 BM forward (SEQ ID NO:7)
- LB26 BM reverse (SEQ ID NO:8)

What is claimed is:

1. Method of preparing selenium-enriched biomass having a Se-methionine content of at least 11.39 ng/$mg_{d.w.}$, wherein said biomass is obtained by (i) culturing microorganisms selected from the group consisting of *Lactobacillus reuteri* DSM 16143*, Lactobacillus ferintoshensis* DSM 16144 and *Lactobacillus buchneri/parabuchneri* DSM 16341 and combinations thereof in a nutrient culture medium comprising a selenium salt, such that the said microorganisms accumulate selenium; and (ii) separation of the selenium-enriched microorganisms from the culture medium.

2. Method according to claim 1, in which the microorganisms separated from the culture medium are further submitted to an operation of lyophilization or drying to obtain a lyophilized or dried selenium-enriched biomass.

3. Method according to claim 1, in which the selenium salt is selenite.

4. Method according to claim 1, in which the culture medium is a liquid medium.

5. Method according to claim 1, in which the culture medium comprises nutrients for the growth of said microorganisms, selected from the group consisting of inorganic salts, sources of carbon, of nitrogen, of vitamins, of trace elements and mixtures thereof.

6. Method according to claim 1, in which said culture medium has a pH in the range from 2.5 to 8.

7. Method according to claim 1, in which said microorganisms are cultured in said culture medium at a temperature in the range from 25 to 45° C.

8. Method according to claim 1, in which said microorganisms are cultured in said culture medium for 6 to 40 hours.

9. Method according to claim 1, in which said microorganisms are separated from the culture medium by centrifugation or microfiltration.

10. A selenium-enriched biomass obtainable by the method according to claim 1.

11. Biomass according to claim 10, comprising live microorganisms.

12. Biomass according to claim 10, comprising microorganisms selected from the group consisting of *Lactobacillus reuteri* strain LB2 BM deposited at the DSMZ on 17 Jan. 2004 under accession number DSM 16143*, Lactobacillus ferintoshensis* strain LB6 BM deposited at the DSMZ on 17 Jan. 2004 under accession number DSM 16144, *Lactobacillus buchneri/parabuchneri* strain LB26 BM deposited at the DSMZ on 5 Apr. 2004 under accession number DSM 16341, and combinations thereof.

13. A composition having probiotic activity containing selenium-enriched biomass according to claim 10 in combination with suitable vehicles and/or excipients.

14. Composition according to claim 13, having a bacterial load of at least $10^9$ CFU/g.

15. A food preparation, food supplement and nutraceutical product comprising a composition having probiotic activity according to claim 13.

16. An isolated microorganism selected from the group consisting of *Lactobacillus reuteri* strain LB2 BM deposited at the DSMZ on 17 Jan. 2004 under accession number DSM 16143, *Lactobacillus ferintoshensis* strain LB6 BM deposited at the DSMZ on 17 Jan. 2004 under accession number DSM 16144 and *Lactobacillus buchneri/parabuchneri* strain LB26 BM deposited at the DSMZ on 5 Apr. 2004 under accession number DSM 16341.

17. Method according to claim 6, in which said culture medium has a pH in the range from 3.5 to 7.5.

18. Method according to claim 7, in which said microorganisms are cultured in said culture medium at a temperature in the range from 32 to 40° C.

19. Method according to claim 8, in which said microorganisms are cultured in said culture medium for 8 to 36 hours.

* * * * *